US008293229B2

(12) United States Patent
Ortenzi et al.

(10) Patent No.: US 8,293,229 B2
(45) Date of Patent: Oct. 23, 2012

(54) METHODS OF PRODUCING STABLE PANCREATIC ENZYME COMPOSITIONS

(75) Inventors: Giovanni Ortenzi, Monza (IT); Marco Marconi, Balsamo (IT); Luigi Mapelli, Milan (IT)

(73) Assignee: Aptalis Pharma Limited, Wicklow (IE)

( * ) Notice: Subject to any disclaimer, the term of this patent is extended or adjusted under 35 U.S.C. 154(b) by 1106 days.

(21) Appl. No.: 12/034,491

(22) Filed: Feb. 20, 2008

(65) Prior Publication Data

US 2008/0279953 A1 Nov. 13, 2008

Related U.S. Application Data

(60) Provisional application No. 60/902,091, filed on Feb. 20, 2007, provisional application No. 60/902,093, filed on Feb. 20, 2007, provisional application No. 60/902,092, filed on Feb. 20, 2007.

(51) Int. Cl.
*A61K 9/14* (2006.01)

(52) U.S. Cl. ............. 424/94.6; 424/490; 424/94.2

(58) Field of Classification Search ................. None
See application file for complete search history.

(56) References Cited

U.S. PATENT DOCUMENTS

| | | | |
|---|---|---|---|
| 4,079,125 A | 3/1978 | Sipos | |
| 4,704,295 A | 11/1987 | Porter et al. | |
| 4,786,505 A | 11/1988 | Lovgren et al. | |
| 5,225,202 A | 7/1993 | Hodges et al. | |
| 5,260,074 A * | 11/1993 | Sipos | 424/497 |
| 5,306,506 A * | 4/1994 | Zema et al. | 424/466 |
| 5,324,514 A * | 6/1994 | Sipos | 424/94.63 |
| 5,378,462 A | 1/1995 | Boedecker et al. | |
| 5,460,812 A | 10/1995 | Sipos | |
| 5,578,304 A | 11/1996 | Sipos | |
| 5,733,575 A | 3/1998 | Mehra et al. | |
| 5,750,104 A * | 5/1998 | Sipos | 424/94.21 |
| 5,861,177 A | 1/1999 | Atzl et al. | |
| 6,313,102 B1 | 11/2001 | Colaco et al. | |
| 6,352,974 B1 | 3/2002 | Ghirri et al. | |
| 6,607,747 B2 | 8/2003 | Ullah et al. | |
| 6,855,336 B2 | 2/2005 | Chen et al. | |
| 6,955,903 B2 | 10/2005 | Kulkarni et al. | |
| 7,201,923 B1 * | 4/2007 | van Lengerich | 424/499 |
| 7,658,918 B1 | 2/2010 | Ortenzi et al. | |
| 2001/0024660 A1 | 9/2001 | Ullah et al. | |
| 2002/0044968 A1 | 4/2002 | van Lengerich | |
| 2004/0101562 A1 | 5/2004 | Maio | |
| 2005/0019417 A1 | 1/2005 | Ko et al. | |
| 2008/0199448 A1 | 8/2008 | Ross et al. | |
| 2008/0274174 A1 | 11/2008 | Ortenzi et al. | |
| 2008/0279839 A1 | 11/2008 | Schuler et al. | |
| 2008/0299185 A1 | 12/2008 | Ortenzi et al. | |
| 2009/0117180 A1 | 5/2009 | Ortenzi et al. | |
| 2009/0232789 A1 | 9/2009 | Fallon | |
| 2010/0021537 A1 | 1/2010 | Ortenzi et al. | |
| 2010/0270183 A1 | 10/2010 | Ortenzi et al. | |
| 2011/0123605 A1 | 5/2011 | Ortenzi et al. | |
| 2011/0123633 A1 | 5/2011 | Ortenzi et al. | |
| 2011/0123634 A1 | 5/2011 | Ortenzi et al. | |

FOREIGN PATENT DOCUMENTS

| | | |
|---|---|---|
| CA | 2 263 703 A1 | 8/1999 |
| CN | 87103560 A | 5/1988 |
| CN | 1489476 A | 4/2004 |
| DE | 199 07 764 A1 | 11/1999 |
| EP | 0 283 442 A1 | 9/1988 |
| EP | 0283442 A1 | 9/1988 |
| EP | 0 576 938 A1 | 1/1994 |
| EP | 0879772 A2 | 11/1998 |
| FR | 2 313 916 A1 | 1/1977 |
| WO | WO 87/05505 A1 | 9/1987 |
| WO | WO 02/40045 A2 | 5/2002 |
| WO | WO 02/058735 A1 | 8/2002 |
| WO | WO 2006/044529 A1 | 4/2006 |
| WO | WO 2007/013752 A1 | 2/2007 |
| WO | WO 2007/020259 A2 | 2/2007 |
| WO | WO 2007/020260 A2 | 2/2007 |

OTHER PUBLICATIONS

Boulois, Denis, "International Search Report," 5 pages, from International Application No. PCT/IB2008/000770, filed Feb. 20, 2008, European Patent Office, Rijswijk, The Netherlands (mailed Jun. 3, 2009).

International Preliminary Report on Patentability based on International Application No. PCT/IB2008/000770 (Sep. 3, 2009).

Hageman, "The role of moisture in protein stability," Drug Dev. Ind. Pharm. 14(14):2047-2070 (1988).

Maul and Schmidt, "Influence of different-shaped pigments on bisacodyl release from Eudragit L30D," Int. J. Pharm. 118:103-112 (1995).

Maul and Schmidt, "Influence of different-shaped pigments and plasticizers on theophylline release from Eudragit RS3OD and Aquacoat ECD30 coated pellets," S.T.P. Pharma Sciences 7(6):498-506 (1997).

Felton and McGinity, "Influence of insoluble excipients on film coating systems," Drug Dev. Ind. Pharm. 28(3):225-243 (2002).

Parker et al., "Effects of solids-loading on mositure permeability coefficients of free films," J. Pharm. Sci. 63(1):119-125 (1974).

Thoma and Bechtold, "Influence of aqueous coatings on the stability of enteric coated pellets and tablets," Eur. J. Pharm. Biopharm. 47:39-50 (1999).

Nordmark pancreatin brochure (publication year unknown), available at http://www.nordmark-pharma.de/english/download.html (webpage © 2004).

Krishnamurty et al., "Delayed release pancrelipase for treatment of pancreatic exocrine insufficiency associated with chronic pancreatitis," Ther. Clin. Risk. Manage. 5:507-520 (2009).

(Continued)

*Primary Examiner* — Hope Robinson

(74) *Attorney, Agent, or Firm* — Cooley LLP

(57) ABSTRACT

Compositions of the present invention, comprising at least one digestive enzyme (e.g., pancrelipase) are useful for treating or preventing disorders associated with digestive enzyme deficiencies. The compositions of the present invention can comprise a plurality of coated particles, each of which is comprised of a core coated with an enteric coating comprising at least one enteric polymer and 4-10% of at least one alkalinizing agent, or have moisture contents of about 3% or less, water activities of about 0.6 or less, or exhibit a loss of activity of no more than about 15% after six months of accelerated stability testing.

20 Claims, No Drawings

OTHER PUBLICATIONS

Drugs@FDA Glossary of Terms, printed Nov. 20, 2009, 7 pages: http://www.fda.gov/Drugs/InformationonDrugs/ucm079436.htm.
U.S. Department of Health and Human Services, Food and Drug Administration, Center for Veterinary Medicine, Guidance for Industry #191, Released Nov. 19, 2009: Changes to Approved NADAs—*New NADAs* vs. *Category II Supplemental NADAs*, Final Guidance, 25 pages.
Krenn, "Written Opinion," 6 pages, Singapore patent appl. No. 200905385-1, Austrian Patent Office (Dec. 16, 2010).

* cited by examiner

METHODS OF PRODUCING STABLE PANCREATIC ENZYME COMPOSITIONS

CROSS-REFERENCE TO RELATED APPLICATIONS

The present application claims priority to U.S. Provisional Application No. 60/902,091 filed Feb. 20, 2007, U.S. Provisional Application No. 60/902,093 filed Feb. 20, 2007, and U.S. Provisional Application No. 60/902,092 filed Feb. 20, 2007, the disclosures of which are each herein incorporated by reference in their entirety for all purposes.

BACKGROUND OF THE INVENTION

In cases of pancreatic insufficiency, pancrelipase and other pancreatic enzymes products (PEPs) can be administered to at least partially remedy the enzyme deficiency caused by various diseases affecting the pancreas, such as pancreatitis, pancreatectomy, cystic fibrosis, etc. The use of pancreatic enzymes in the treatment of pancreatic insufficiency is an essential part of the therapy of patients afflicted with cystic fibrosis. Without these supplements, patients become severely nutritionally impaired. This nutritional impairment can be life threatening if left untreated, particularly in the case of infants.

The drug substance pancrelipase is mainly a combination of three enzyme classes: lipase, protease and amylase, together with their various co-factors and co-enzymes. These enzymes are produced naturally in the pancreas and are important in the digestion of fats, proteins and carbohydrates. Pancrelipase is typically prepared from porcine pancreatic glands, although other sources can also be used, for example those described in U.S. Pat. No. 6,051,220, U.S. 2004/0057944, 2001/0046493, and WO 2006044529, each of which is herein incorporated by reference. The enzymes catalyze the hydrolysis of fats into glycerol and fatty acids, starch into dextrin and sugars, and protein into amino acids and derived substances.

Pancreatic enzymes show optimal activity under near neutral and slightly alkaline conditions. Under gastric conditions, pancreatic enzymes may be inactivated with a resulting loss in biological activity. Therefore, exogenously administered enzymes are generally protected against gastric inactivation and remain intact during their transit through the stomach and into the duodenum. Although it is desirable to coat pancreatic enzymes, uncoated preparations are also found in commerce. Pancreatic lipases are the most sensitive to gastric inactivation and are the most important single enzymes in the treatment of malabsorption. Lipase activity is typically monitored to determine the stability of an enzyme composition containing lipase.

After passage through the stomach, the enzymes should be released in the duodenum within 5-30 minutes, since digestion by pancreatic enzymes and absorption of the metabolites takes place primarily in the upper segment of the intestine, although digestion and absorption can take place throughout GI transit. Pancreatic enzymes have typically been coated with an enteric coating polymer, which protects the enzyme composition against the acidic environment of the stomach and then provides release of the enzyme in the intestine.

The conventional pancreatic enzyme preparations are intrinsically unstable and do not possess the shelf-life typically associated with approved pharmaceutical products for oral use. The activity of pancreatic enzyme preparations is typically determined based on the activity of lipase, which is one of the enzymes most sensitive to losing enzymatic activity during storage. Commercially available digestive enzyme compositions show a loss of lipase activity over time of up to about 35% or more. In order to compensate for the losses of enzymatic activity during storage and to ensure that the product provides the label-claimed potency at the end of the shelf life, manufacturers typically overfill the dosage forms from 5% to 60% and current USP specifications for Pancrelipase Delayed-Release Capsules allow for Pancrelipase equivalent to not less than 90% and not more than 165% of the labeled lipase activity.

In practice this means that patients and prescribers are unable to judge the dosage strength with accuracy, with the practical result that the appropriate dosage needs to be determined empirically for each new prescription. Patients with exocrine pancreatic insufficiency disorders rely on these drugs to provide the enzymes they need to digest food properly. If the label contains an inaccurate statement about a particular product's potency, then the patient is at risk for receiving too much or too little of the medicine.

Accordingly, it would be desirable to provide a stable digestive enzyme composition capable of maintaining the necessary activity for the expected shelf life of the enzyme preparation, without depending on overfilling the dosage form.

SUMMARY OF THE INVENTION

The present invention relates to stable digestive enzyme compositions and dosage forms and methods for producing stable enzyme compositions and dosage forms. More particularly, the present invention relates to enteric coated enzyme compositions and dosage forms that exhibit minimal loss of activity under typical storage conditions.

In one embodiment, the present invention provides a composition comprising at least one digestive enzyme, wherein the composition has a moisture content of about 3% or less.

In another embodiment, a composition of the present invention comprises at least one digestive enzyme, wherein the composition has a water activity of about 0.6 or less.

In another embodiment, a composition of the present invention comprises at least one stabilized digestive enzyme, wherein the at least one stabilized digestive enzyme exhibits a loss of activity of no more than about 15% after six months of accelerated stability testing.

In yet another embodiment, the present invention provides a dosage form such as a tablet or a capsule filled with the composition of the present invention.

In yet another embodiment, a composition of the present invention further comprises the at least one digestive enzyme coated with a coating, wherein the coating comprises an enteric polymer and optionally at least one inorganic material.

In yet another embodiment, the present invention provides a package comprising a sealed container made of moisture resistant material, a desiccant, and at least one dosage form of the present invention, wherein the desiccant and at least one dosage form are inside the sealed container.

In yet another embodiment, the present invention provides a method of treating or preventing a disorder associated with digestive enzyme deficiency comprising administering a composition of the present invention to a mammal in need thereof.

In yet another embodiment, the present invention provides a method of preparing a composition of the present invention. In one embodiment, the method comprises coating particles of the at least one digestive enzyme in an atmosphere having a moisture content of about 3.6 g water per $m^3$ or less, with a coating comprising an enteric polymer and at least one inorganic material, thereby forming a plurality of delayed release particles.

DETAILED DESCRIPTION OF THE INVENTION

One aspect of the present invention is directed to a stabilized digestive enzyme composition. The term "stabilized digestive enzyme" means a digestive enzyme which maintains substantial enzymatic activity after long-term storage. The term "digestive enzyme" denotes an enzyme in the alimentary tract which breaks down the components of food so that they can be taken or absorbed by the organism.

Non-limiting classes of digestive enzymes suitable for use in the present invention include lipases, amylases and proteases. Non-limiting examples of digestive enzymes include pancrelipase (also referred to as pancreatin), lipase, co-lipase, trypsin, chymotrypsin, chymotrypsin B, pancreatopeptidase, carboxypeptidase A, carboxypeptidase B, glycerol ester hydrolase, phospholipase, sterol ester hydrolase, elastase, kininogenase, ribonuclease, deoxyribonuclease, α-amylase, papain, chymopapain, glutenase, bromelain, ficin, β-amylase, cellulase, β-Galactosidase, lactase, sucrase, isomaltase, and mixtures thereof.

In one embodiment of the present invention, the stabilized digestive enzyme is a pancreatic enzyme. The term "pancreatic enzyme" as used herein refers to any one of the enzyme types present in the pancreatic secretion, such as amylase, lipase, protease, or mixtures thereof, or any extractive of pancreatic origin having enzymatic activity, such as pancreatin. The pancreatic enzyme can be obtained through extraction from the pancreas, produced artificially, or obtained from sources other than the pancreas, such as from microbes, plants or other animal tissues.

In another embodiment of the present invention, the stabilized digestive enzyme is pancrelipase. The terms "pancrelipase" or "pancreatin" denote a mixture of several types of enzymes, including amylase, lipase, and protease enzymes. Pancrelipase is commercially available, for example from Nordmark Arzneimittel GmbH, or Scientific Protein Laboratories LLC.

In one embodiment of the compositions of the present invention, the stabilized digestive enzyme comprises a lipase. The term "lipase" refers to an enzyme that catalyzes the hydrolysis of lipids to glycerol and simple fatty acids.

Examples of lipases suitable for the present invention include, but are not limited to animal lipase (e.g., porcine lipase), bacterial lipase (e.g., Pseudomonas lipase and/or Burkholderia lipase), fungal lipase, plant lipase, recombinant lipase (e.g., produced via recombinant DNA technology by a suitable host cell, selected from any one of bacteria, yeast, fungi, plant, insect or mammalian host cells in culture, or recombinant lipases which include an amino acid sequence that is homologous or substantially identical to a naturally occurring sequence, lipases encoded by a nucleic acid that is homologous or substantially identical to a naturally occurring lipase-encoding nucleic acid, etc.), chemically-modified lipase, or mixtures thereof.

In another embodiment of the compositions of the present invention, the stabilized digestive enzyme comprises an amylase. The term "amylase" refers to glycoside hydrolase enzymes that break down starch, for example α-amylases, β-amylases, γ-amylases, acid α-glucosidases, salivary amylases such as ptyalin, etc.

The amylases suitable for use in the compositions of the present invention include, but are not limited to animal amylases, bacterial amylases, fungal amylases (e.g., Aspergillus amylase and, preferably, is Aspergillus oryzae amylase), plant amylases, recombinant amylases (e.g., produced via recombinant DNA technology by a suitable host cell, selected from any one of bacteria, yeast, fungi, plant, insect or mammalian host cells in culture, or recombinant amylases which include an amino acid sequence that is homologous or substantially identical to a naturally occurring sequence, amylases encoded by a nucleic acid that is homologous or substantially identical to a naturally occurring amylase-encoding nucleic acid, etc.), chemically modified amylases, or mixtures thereof.

In another embodiment of the compositions of the present invention, the stabilized digestive enzyme comprises a protease. The term "protease" refers generally to enzymes (e.g., proteinases, peptidases, or proteolytic enzymes) that break peptide bonds between amino acids of proteins. Proteases are generally identified by their catalytic type, e.g., aspartic acid peptidases, cysteine (thiol) peptidases, metallopeptidases, serine peptidases, threonine peptidases, alkaline or semi-alkaline proteases, neutral and peptidases of unknown catalytic mechanism.

Non-limiting examples of proteases suitable for use in the compositions or oral dosage forms of the present invention include serine proteases, threonine proteases, cysteine proteases, aspartic acid proteases (e.g., plasmepsin) metalloproteases, glutamic acid proteases, etc. in addition, proteases suitable for use in the compositions or oral dosage forms of the present invention include, but are not limited to animal proteases, bacterial proteases, fungal proteases (e.g., an Aspergillus melleus protease), plant proteases, recombinant proteases (e.g., produced via recombinant DNA technology by a suitable host cell, selected from any one of bacteria, yeast, fungi, plant, insect or mammalian host cells in culture, or recombinant proteases which include an amino acid sequence that is homologous or substantially identical to a naturally occurring sequence, proteases encoded by a nucleic acid that is homologous or substantially identical to a naturally occurring protease-encoding nucleic acid, etc.), chemically modified proteases, or mixtures thereof.

The compositions or oral dosage forms of the present invention can comprise one or more lipases (i.e., one lipase, or two or more lipases), one or more amylases (i.e., one amylase, or two or more amylases), one or more proteases (i.e., one protease, or two or more proteases), mixtures of one or more lipases with one or more amylases, mixtures of one or more lipases with one or more proteases, mixtures of one or more amylases with one or more proteases, or mixtures of one or more lipases with one or more amylases and one or more proteases.

In one embodiment, the digestive enzyme is a porcine pancreatic extract comprising various lipases (e.g., lipase, colipase, phospholipase A2, cholesterol esterase), proteases (e.g., trypsin, chymotrypsin, carboxypeptidase A and B, elastase, kininogenase, trypsin inhibitor), amylases, and optionally nucleases (ribonuclease, deoxyribonuclease). In another embodiment, the digestive enzyme is substantially similar to human pancreatic fluid. In yet another embodiment, the digestive enzyme is pancrelipase USP. In still another embodiment, the digestive enzyme is pancrelipase ESP having a lipase activity of 69-120 U USP/mg, amylase activity of greater than or equal to 216 U USP/mg, protease activity of greater than or equal to 264 U USP/mg, and total protease activity of greater than or equal to 264 U USP/mg.

Lipase activities in the compositions or oral dosage forms of the present invention can be about 4500-25,000 IU, for example about 4500-5500 IU, about 9000-11,000 IU, about 13,500-16,500 IU, and about 18,000-22,000 IU. Amylase activities in the compositions or oral dosage forms of the present invention can be about 8100-180,000 IU, for example about 8000-45,000 IU, about 17,000-90,000 IU, about 26,000-135,000 IU, about 35,000-180,000 IU. Protease activities in the compositions or oral dosage forms of the present invention can be about 8000-134,000 IU, for example about 8000-34,000 IU, 17,000-67,000 IU, 26,000-100,000 IU, 35,000-134,000 IU. In one embodiment, the lipase activity ranges from about 4500-5500 IU, the amylase activity ranges from about 8000-45,000 IU, and the protease activity ranges from about 8000-34,000 IU. In another embodiment, the lipase activity ranges from about 9000-11,000 IU, the amylase activity ranges from about 17,000-90,000 IU, and the protease activity ranges from about 17,000-67,000 IU. In yet another embodiment, the lipase activity ranges from about 13,500-16,500 IU, the amylase activity ranges from about 26,000-135,000 IU, and the protease activity ranges from about 26,000-100,000 IU. In still another embodiment, the lipase activity ranges from about 18,000-22,000 IU, the amylase activity ranges from about 35,000-180,000 IU, and the protease activity ranges from about 35,000-134,000 IU.

The ratios of lipase:protease:amylase in the compositions or oral dosage forms of the present invention can be in the range of about 1:10:10 to about 10:1:1, or about 1.0:1.0:0.15 (based on enzyme activities). The ratio of amylase/lipase in the compositions or oral dosage forms of the present invention can range from about 1.8-8.2, for example about 1.9-8.2, and about 2.0-8.2. The ratio of protease/lipase in the compositions or oral dosage forms of the present invention can range from about 1.8-6.2, for example about 1.9-6.1, and about 2.0-6.1.

In another embodiment, the activities of lipase, protease, and amylase can be those described in Table A, below:

TABLE A

| | Formulation | | | | | | | |
|---|---|---|---|---|---|---|---|---|
| | 1 | | 2 | | 3 | | 4 | |
| | min | max | min | max | min | max | min | max |
| Activity (IU) | | | | | | | | |
| Lipase | 4500 | 5500 | 9000 | 11000 | 13500 | 16500 | 18000 | 22000 |
| Amylase | 8100 | 45000 | 17100 | 90000 | 26100 | 135000 | 35100 | 180000 |
| Protease | 8100 | 34000 | 17100 | 67000 | 26100 | 100000 | 35100 | 134000 |
| Ratio | | | | | | | | |
| Amylase/Lipase | 1.8 | 8.2 | 1.9 | 8.2 | 1.9 | 8.2 | 2.0 | 8.2 |
| Protease/Lipase | 1.8 | 6.2 | 1.9 | 6.1 | 1.9 | 6.1 | 2.0 | 6.1 |

The total amount of digestive enzymes (by weight) in the compositions or oral dosage forms of the present invention can be about 20-100%, 20-90%, 20-80%, 20-70%, 20-60%, 20-50%, 20-40%, 20-30%, or about 20%, about 30%, about 40%, about 50%, about 60%, about 70%, about 80%, about 90%, or about 100%. In one embodiment, the total amount of digestive enzymes is 60-90%. In another embodiment, the total amount of digestive enzymes (e.g., pancrelipase) is about 68-72%.

In one embodiment, the compositions or oral dosage forms of the present invention, comprising at least one digestive enzyme, have a moisture content of about 3% or less, about 2.5% or less, about 2% or less, about 1.5% or less, or about 1% or less, inclusive of all ranges and subranges therebetween (i.e., any of about 2.5% to 3%, 2% to 3%, 1.5% to 3%, 1% to 3%, 2% to 2.5%, 1.5% to 2.5%, 1% to 2.5%, 1.5% to 2%, 1% to 2%, 1% to 1.5%, etc.). Compositions or oral dosage forms of the present invention, maintained at low moisture content, have been found to be substantially more stable compared to conventional compositions maintained at higher moisture contents, e.g. above about 3% or higher.

The term "moisture content", also referred to as "water content", means the amount of water that a composition contains. For compositions which do not change volume with changing moisture content, the moisture content can be expressed volumetrically (i.e., by volume) as the ratio of the mass of moisture to the dry volume of the material. For compositions that change volume with changing moisture content, the moisture content can be expressed gravimetrically (i.e., by weight) as the mass of water removed upon drying per unit dry mass of the specimen. Determination of moisture content can be achieved by any of the conventional methods known in the art. For example, the moisture content can be determined by chemical titration, such as Karl Fischer titration, in which a sample is dissolved in an electrochemical titration cell. Water from the sample is consumed in an electrochemical reaction whose endpoint is measured potentiometrically, thereby providing a direct measure of the amount of water in the sample. Alternatively, relatively simple thermogravimetric methods may be used such as "Loss on Drying" (LoD), in which the mass of a sample is measured prior to, and after controlled drying. The loss of mass after drying is attributed to loss of moisture. Commercially available moisture analyzers (e.g., available from Mettler Toledo, Sartorius AG, etc.) can also be used to determine moisture content. The moisture content of the compositions or oral dosage forms of the present invention can be measured by any suitable method known in the art, for example LoD.

In another embodiment, the compositions or oral dosage forms of the present invention, comprising at least one digestive enzyme, have a water activity of about 0.6 or less, about 0.5 or less, about 0.4 or less, about 0.3 or less, about 0.2 or less, or about 0.1 or less, inclusive of all ranges and subranges therebetween (i.e., any of about 0.5 to 0.6, 0.4 to 0.6, 0.3 to 0.6, 0.2 to 0.6, 0.1 to 0.6, 0.4 to 0.5, 0.3 to 0.5, 0.2 to 0.5, 0.1 to 0.5, 0.3 to 0.4, 0.2 to 0.4, 0.1 to 0.4, 0.2 to 0.3, 0.1 to 0.3, 0.1 to 0.2, etc.). Compositions or oral dosage forms of the present invention, maintained at a low water activity, have been found to be substantially more stable compared to conventional digestive enzyme compositions maintained at higher water activity levels.

Water activity, also referred to as "aw", is the relative availability of water in a substance. As used herein, the term "water activity" is defined as the vapor pressure of water in a sample divided by the vapor pressure of pure water at the same temperature. Pure distilled water has a water activity of exactly one. Water activity is temperature dependent. That is, water activity changes as the temperature changes. In the present invention, water activity is measured at a temperature ranging from about 0° C. to about 50° C., preferably from about 10° C. to about 40° C.

The water activity of a product can be determined by measuring the relative humidity of the air surrounding the sample at equilibrium. Accordingly, measurement of water activity in a sample is typically carried out in an enclosed (usually insulated) space where this equilibrium can take place. At equilibrium, the water activity of the sample and the relative humidity of the air are equal, and therefore a measurement of the equilibrium relative humidity (ERH) of the air in the chamber provides a measure of the water activity of the sample. At least two different types of water activity instruments are commercially available. One type of water activity instruments uses chilled-mirror dewpoint technology (e.g., AquaLab™ water activity meters available from Decagon Devices, Inc.) while others measure relative humidity with sensors that change electrical resistance or capacitance (e.g., water activity meters available from Rotronic). The water activity of the compositions or oral dosage forms of the present invention can be measured by any suitable method known in the art.

In another embodiment, the compositions or oral dosage forms of the present invention, comprising at least one stabilized digestive enzyme, exhibit a loss of enzyme activity of no more than about 25%, no more than about 20%, no more than about 15%, no more than about 12%, no more than about 10%, no more than about 8%, or no more than about 5%, after six months of accelerated stability testing.

The term "accelerated stability testing" or "accelerated storage testing" refers to test methods used to simulate the effects of relatively long-term storage conditions on enzyme activity, which can be carried out in a relatively short time. Accelerated stability testing methods are known in the art to be a reliable alternative to real-time stability testing, and can accurately predict the shelf life of biological products. Such "accelerated stability testing" conditions are known in the art and are in accordance with the International Conference for Harmonization of Technical Requirements for Registration of Pharmaceuticals for Human Use: Stability Testing of New Drug Substances and Products Q1A, herein incorporated by reference in its entirety.

One method of accelerated stability testing comprises storing samples of digestive enzyme composition in a sealed Nialene (nylon, aluminium, polyethylene laminate; GOGLIO SpA, Milan) bag at 40° C./75% relative humidity for 6 months.

After storage (or periodically during storage) the enzyme activity of the samples can be tested using conventional methods for assaying digestive enzyme activity (e.g., United States Pharmacopoeia, Pancrelipase: Assay for lipase activity; herein incorporated by reference in its entirety).

The compositions or oral dosage forms of the present invention can also further comprise one or more stabilizers which enhance or improve the stability of the compositions or oral dosage forms of the present invention. Non-limiting examples of suitable stabilizers include proline, trehalose, dextran, maltose, sucrose, mannitol, polyols, silica gel, aminoguanidine, pyridoxamine, anhydrous metal salts, such as sodium hydrogen carbonate magnesium oxide, calcium oxide, aluminium oxide and mixtures thereof. The one or more stabilizers can have a moisture content of about 3% or less and/or a water activity of 0.6 or less.

Non-limiting examples of suitable forms of trehalose which can be used in the compositions or oral dosage forms of the present invention include trehalose dihydrate (TD), amorphous trehalose (AT), anhydrous trehalose (e.g. anhydrous amorphous trehalose (AAT), anhydrous crystalline trehalose (ACT)). Powdered anhydrous trehalose may contain any AAT and/or ACT. As used herein, the term "trehalose" refers to any physical form of trehalose, including anhydrous, partially hydrated, fully hydrated and mixtures and solutions thereof. The term "anhydrous trehalose" refers to any physical form of trehalose containing less than 2% water. The anhydrous forms of trehalose may contain from 0-2% water. Amorphous trehalose contains about 2-9% water and trehalose dihydrate contains about 9-10% water. Anhydrous trehalose can be prepared as described in PCT/GB97/00367, herein incorporated by reference in its entirety. In one embodiment, the compositions or oral dosage forms of the present invention comprise one or more stabilized digestive enzymes and anhydrous trehalose.

The amount of anhydrous trehalose (AAT or ACT) in the composition of the present invention can be in the range of about 5-50%, 5-40%, 5-30%, 5-20%, 5-15%, 5-10%, 7-15%, or about 5%, about 7%, about 10%, about 15%, or about 20%.

The anhydrous trehalose can be incorporated into the compositions or oral dosage forms of the present invention as a powder. The particle size of the anhydrous trehalose powder can be in the range of about 2-2000 µm.

Compositions or oral dosage forms of the present invention comprising one or more stabilized digestive enzymes and anhydrous trehalose confer improved enzyme stability. It is believed that the anhydrous trehalose stabilizes the compositions or oral dosage forms of the present invention by absorbing or sequestering moisture from ambient humidity, or residual moisture from manufacturing or within the formulation itself.

Depending on the intended use and requirement of the compositions, the weight ratio of the stabilized digestive enzyme to the stabilizer ranges from about 99:1 to 80:20. The stabilizer can be incorporated into the compositions or oral dosage forms of the present invention by wet or dry blending at least one stabilized digestive enzyme with at least one stabilizer. In one embodiment, one or more stabilized digestive enzyme is dry blended with one or more stabilizer. In another embodiment, one or more stabilized digestive enzyme is wet blended with one or more stabilizer.

In addition to the stabilized digestive enzyme and/or stabilizer(s), the compositions or oral dosage forms of the present invention can further comprise one or more pharmaceutically acceptable excipients. The term "excipients" includes other pharmaceutically acceptable ingredients added to the active component(s) of a composition (e.g., the stabilized digestive enzymes) in order to improve processing, stability, palatability, etc. Non-limiting examples of suitable excipients include pharmaceutically acceptable binders, stabilizers, disintegrants, lubricants, glidants, diluents, and mixtures thereof etc. It will be appreciated by those skilled in the art of pharmaceutical formulations that a particular excipient may carry out multiple functions in the composition. So, for example a binder may also function as a diluent, etc. The excipients can have a moisture content of about 3% or less and/or a water activity of about 0.6 or less.

Non-limiting examples of suitable binders include starches, sugars (e.g. lactose), sugar alcohols (e.g. xylitol, sorbitol, maltitol), cellulose (e.g. microcrystalline cellulose), modified celluloses (e.g., hydroxypropylcellulose, carboxymethylcellulose sodium), alginic acid, polyvinyl pyrrolidone (povidone), and mixtures thereof. Non-limiting examples of suitable disintegrants include dibasic calcium phosphate, dibasic calcium phosphate dihydrate, tribasic calcium phosphate, alginic acid, hydroxypropylcellulose, carboxymethylcellulose calcium, carboxymethylcellulose sodium, cross-linked carboxymethylcellulose sodium, swellable ion exchange resins, alginates, formaldehyde-casein, cellulose, croscarmellose sodium, crospovidone (e.g., cross-linked polyvinyl pyrrolidone), microcrystalline cellulose, sodium carboxymethyl starch, sodium starch glycolate, starches (corn starch, rice starch), and mixtures thereof. Non-limiting examples of suitable lubricants include calcium stearate, magnesium stearate, sodium stearyl fumarate, stearic acid, zinc stearate, talc, waxes, Sterotex®, Stearowet®, and mixtures thereof. Non-limiting examples of suitable glidants include colloidal silicon dioxide, talc, and mixtures thereof. Non-limiting examples of suitable diluents include mannitol, sucrose, anhydrous dibasic calcium phosphate, anhydrous dibasic calcium phosphate dihydrate, tribasic calcium phosphate, cellulose, lactose, magnesium carbonate, microcrystalline cellulose, and mixtures thereof. Non-limiting examples of suitable stabilizers include trehalose, proline, dextran, maltose, sucrose, mannitol, polyols, silica gel, aminoguanidine, pyridoxamine, and mixtures thereof.

In one embodiment, the disintegrant is crospovidone (e.g., POLYPLASDONE XL, POLYPLASDONE XL-10). In another embodiment, the disintegrant is croscarmellose sodium (e.g., AC-DI-SOL). In another embodiment, the disintegrant is sodium starch glycolate (e.g., EXPLOTAB, EXPLOTAB CV). In another embodiment, the compositions or oral dosage forms of the present invention can comprise a combination of disintegrants such as microcrystalline cellulose and sodium starch glycolate or croscarmellose sodium and crospovidone.

The amount of disintegrant can be in the range of about any of about 0.1-30%, 1%-30%, 1%-25%, 1%-20%, 1%-15%, 1%-10%, 1%-5%, 5%-10%, 5%-15%, 5%-20%, 5%-25%, or 5%-30%. In one embodiment, the amount of disintegrant is about 2%-4%, or about 2%-3%, or about 2.5%.

Non-limiting examples of suitable diluents include microcrystalline cellulose, starch, calcium phosphate, lactose, sucrose, mannitol, sorbitol, and combinations thereof. In one embodiment, the diluent is microcrystalline cellulose (e.g. Avicel). In another embodiment, the diluent is starch. In another embodiment, the diluent is lactose (e.g., Pharmatol). In another embodiment, the compositions or oral dosage forms of the present invention can comprise a combination of diluents such as microcrystalline cellulose, starch and lactose.

The amount of diluent can be in the range of about any of about 0.1-99%, 1%-30%, 1%-25%, 1%-20%, 1%-15%, 1%-10%, 1%-5%, 5%-10%, 5%-15%, 5%-20%, 5%-25%, or 5%-30%. In one embodiment, the amount of diluent is about 2%-5%, 3%-5%, or about 4%.

One or more of the excipients of the compositions or oral dosage forms of the present invention can function as a dessicant to further stabilized the composition. Suitable excipients useful as desiccants include any pharmaceutically acceptable excipient that binds water tightly, or reduces the water activity of a composition. For example, the composition of the present invention can include about 1-4% silica gel, or about 2.5% silica gel.

The compositions of the present invention can be prepared in any suitable oral dosage form. Non-limiting examples of suitable dosage forms include tablets, capsules or sachets. Since certain digestive enzymes, such as pancreatic lipases may need to be protected against gastric inactivation prior to release in the duodenum, it is may be desirable that the stabilized digestive enzyme compositions or oral dosage forms of the present invention be provided as a controlled or delayed release formulation. Such controlled or delayed release formulations can include tablets or particles coated with an enteric coating which serves to protect pH-sensitive digestive enzymes from gastric inactivation, yet which releases the digestive enzymes in the duodenum. Alternatively, the controlled release formulations can include capsules filled with the stabilized digestive enzyme compositions or oral dosage forms of the present invention, whereby the capsule protects the contents against gastric inactivation, yet releases the digestive enzymes in the duodenum. However, the stabilized digestive enzyme compositions or oral dosage forms of the present invention are not limited to digestive enzymes susceptible to gastric inactivation, for example certain digestive enzymes that are naturally stable in the gastric environment such as gastric lipases, a range or proteases, including those of pancreatic origin and amylases. Certain digestive enzymes derived or extracted from microorganisms that have an intrinsic stability, or that have been chemically modified by cross-linking.

When the compositions of the present invention are formulated as tablets, the stabilized digestive enzyme(s) can be "tabletted" (i.e., formed into tablets) using methods known in the art, and subsequently coated with an enteric coating, again using methods known in the art.

When the compositions of the present invention are formulated as capsules, the contents of the capsule can be formulated using methods known in the art. For example, the stabilized digestive enzyme composition can be provided in the form of particles or tablets suited to incorporation in a capsule.

The term "particles" as used herein includes fine powders (having particle diameters in the range of about 1 μm) up to pellets having a diameter of about 5 mm.

The stabilized digestive enzyme composition can also be formed into particles coated with a coating, wherein the coating comprises an enteric polymer. The term "enteric polymer" means a polymer that protects the digestive enzymes from gastric contents, for example a polymer that is stable at acidic pH, but can break down rapidly at higher pH or a polymer whose rate of hydration or erosion is slow enough to ensure that contact of gastric contents with the digestive enzymes is relatively minor while it is in the stomach, as opposed to the remainder of the gastro-intestinal tract. Non-limiting examples of enteric polymers include those known in the art, such as modified or unmodified natural polymers such as cellulose acetate phthalate, hydroxypropylmethylcellulose phthalate, hydroxypropylmethylcellulose acetate succinate, and shellac; or synthetic polymers such as acrylic polymers or copolymers methacrylic acid polymers and copolymers, methylmethacrylate copolymers, and methacrylic acid/methylmethacrylate copolymers.

The enteric polymer coating can be a synthetic polymer, optionally including an inorganic material, such as an alkalinizing agent. The resulting coated particles provide delayed release beads comprising a core which comprises the stabilized digestive enzyme(s) and an enteric coating encapsulating the core. The coated stabilized digestive enzyme particles can then be formulated into tablets or capsules.

The enteric polymer and the at least one inorganic material impart enteric properties to the coating of the present invention. That is, when used as a medication, the coating will act as a barrier protecting the medication from the acidic environment of the stomach and substantially prevent the release of the medication before it reaches the small intestine (i.e., the release of enzyme in the stomach is less than about 10-20% of the total amount of enzyme in the composition).

The inorganic material can include, for example, an alkalinizing agent. Non-limiting examples of alkalinizing agents include silicon dioxide, sodium salts, calcium salts, magnesium salts, aluminum salts, aluminum hydroxides, calcium hydroxides magnesium hydroxides, talc, and combinations thereof. In one embodiment, the alkalinizing agent is talc.

Depending on the intended use of the composition, the ratio of the enteric polymer and the at least one inorganic material may be in a range of from about 10:1 to about 1:60 by weight. In another embodiment, the ratio of the enteric polymer and the at least one inorganic material ranges from about 8:1 to about 1:50 by weight. In another embodiment, the ratio of the enteric polymer and the at least one inorganic material ranges from about 6:1 to about 1:40 by weight. In another embodiment, the ratio of the enteric polymer and the at least one inorganic material ranges from about 5:1 to about 1:30 by weight. In another embodiment, the ratio of the enteric polymer and the at least one inorganic material ranges from about 4:1 to about 1:25 by weight. In another embodiment, the ratio of the enteric polymer and the at least one inorganic material ranges from about 4:1 to about 1:9 by weight. In another embodiment, the ratio of the enteric polymer and the at least one inorganic material ranges from about 10:4 to about 10:7 by weight.

In one embodiment, the compositions or oral dosage forms of the present invention comprise stabilized digestive enzyme particles coated with an enteric coating comprising an enteric polymer and an inorganic material such as talc. In a particular embodiment, the inorganic material of the enteric coating comprises about 1-10% by weight of the weight of the total weight of the particles. In another embodiment the inorganic material comprises about 3, about 5, about 7, or about 10% by weight of the particles. In still other embodiments, the inorganic material is an alkalinizing agent and comprises about 20-60% of the dry coating weight. In still other embodiments, the alkalinizing agent is about 25%, about 30%, about 35%, about 40%, about 45%, about 50%, or about 55% of the dry coating weight (inclusive of all ranges, subranges, and values therebetween). In a particular embodiment, the alkalinizing agent is talc. In still another particular embodiment, the dry coating of the particles comprises about 35% talc.

In another embodiment of the present invention, the coating further comprises a plasticizer. Examples of suitable plasticizers include, but are not limited to triacetin, tributyl citrate, tri-ethyl citrate, acetyl tri-n-butyl citrate, diethyl phthalate, dibutyl sebacate, polyethylene glycol, polypropylene glycol, castor oil, acetylated mono-glyceride, acetylated di-glyceride, and mixtures thereof.

The dosage forms of the present invention can be capsules containing the composition of the present invention (e.g., controlled-release particles of the stabilized digestive enzyme composition, coated with an enteric polymer and an alkalinizing agent). The capsules themselves can be comprised of any conventional biodegradable material known in the art, for example, gelatin, polysaccharides such as pullulan, or modified cellulosic materials such as hydroxypropylmethylcellulose. In order to improve the stability of the stabilized digestive enzymes, the capsule can be dried prior to filling, or a capsule comprised of a low moisture content material can be selected. In one embodiment of the dosage form of the present invention, the capsule is comprised of hydroxypropylmethylcellulose. In another embodiment of the dosage form of the present invention, the capsule is comprised of hydroxypropylmethylcellulose having a water content of about 6% or less, for example about any of 4% or less, 2% or less, or 2-6%, or 4-6%. In another embodiment, the capsule is comprised of hydroxypropylmethylcellulose having a water content of less than about 2%.

The dosage forms of the present invention can comprise a single digestive enzyme, or mixtures of digestive enzymes. If the stabilized digestive enzyme composition is formed into particles coated with an enteric coating, the coated particles can each contain a core comprising a single digestive enzyme or mixtures of digestive enzymes. The dosage form can also comprise coated particles, each of which has nominally the same composition, or it can comprise mixtures of different kinds of coated particles. For example the dosage form can be a capsule filled with coated particles, wherein each of the coated particles has a core comprising pancrelipase. Alternatively, the dosage form can be a capsule filled with coated particles, wherein some of the coated particles have a core comprising pancrelipase, whereas other coated particles have cores comprising a different lipase, or proteases or amylases. Any suitable combination of coated particles of different compositions can be used to provide the desired therapeutic effect.

In addition, when the dosage forms of the present invention are comprised of coated particles of stabilized digestive enzymes, the individual particles can each have the same coating composition, or can include mixtures of particles, some of which have a different coating composition. Any suitable combination of coating compositions can be used to provide the desired type of controlled release or therapeutic effect.

The core of the coated particles can have any suitable particle size or shape. For example, the coated particles can be in the form of a coated powder having a particle size range of about 50-5000 microns, or can be in the form of "minitabs" which have a nominal particle diameter in the range of about 2-5 mm. For other applications, the core of the coated particles can be "microtabs" which have nominal particle diameters of less than about 2 mm, for example about 1-2 mm.

In one embodiment, the compositions or oral dosage forms of the present invention can comprise a plurality of coated digestive enzyme particles (e.g., pancrelipase). The digestive enzyme particles can comprise a digestive enzyme, at least one disintegrant, at least one polymeric binder or diluent, and optionally at least one plasticizer, optionally at least one glidant, and optionally at least one lubricant. In one embodiment, the digestive enzyme particles can comprise about 60-90% of digestive enzyme, about 1-4% of at least one disintegrant, about 2-6% of at least one polymeric binder or diluent, and optionally about 0.5-1.0% of at least one plasticizer, optionally about 0.2-0.6% of at least one glidant, and optionally about 0.2-0.6% of at least one lubricant. For example, the digestive enzyme particles can comprise about 60-90% pancrelipase, about 1-4% of croscarmellose sodium, about 0.5-1.0% of hydrogenated castor oil, about 0.2-0.6% of colloidal silicon dioxide, about 2-6% of microcrystalline cellulose, and about 0.2-0.6% of magnesium stearate. The coating can comprise at least one enteric polymer, about 4-10% of at least one alkalinizing agent (based on the total weight of the particles), and optionally at least one plasticizer. In one embodiment, the coating can comprise about 10-20% of a least one enteric polymer, about 4-10% of a least one alkalinizing agent, and about 1-2% of a least one plasticizer (based on the total weight of the particles). For example, the coating can comprise about 10-20% of hydroxypropylmethylcellulose phthalate, about 4-10% of talc, and about 1-2% of triethyl citrate (based on the total weight of the particles). The plurality of coated digestive enzyme particles can then be formed into a tablet, or filled into a capsule. In one embodiment, the capsule comprises hydroxypropylmethylcellulose.

The compositions of the present invention, and dosage forms comprising the compositions of the present invention, have improved stability compared to conventional digestive enzyme (e.g., pancrelipase) compositions and dosage forms. Consequently, the dosage forms of the present invention do not require "overfilling" (i.e., zero-overfill), as do conventional digestive enzyme dosage forms, to deliver a clinically useful amount of digestive enzyme to a patient in need thereof. Conventional digestive enzyme compositions and dosage forms require overfilling levels of as much as 65% (i.e., 165% of the required dose of digestive enzyme) to compensate for the poor enzyme stability. As a result, there is uncertainty as to the dose delivered by conventional digestive enzyme compositions. Thus, conventional "overfilled" dosage forms can deliver higher than the intended dose of digestive enzymes shortly after manufacture, but over time, the enzyme activity can fall below the intended dose.

In one embodiment, the dosage forms comprising the compositions of the present invention are substantially zero-overfill. The term "substantially zero-overfill" means compositions of the present invention in which the amount of additional digestive enzyme activity (i.e., the amount of additional enzyme activity above the intended dose) is less than or equal to about 10%, i.e., about 10%, less than about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 2%, less than or equal to about 1%, or about 0%. So, for example, if the intended dose is about 4500 IU lipase, the substantially zero-overfill dosage forms of the present invention may contain less than or equal to about 4950 IU lipase (i.e., less than or equal to 110% of 4500 IU lipase). In another embodiment, the zero-overfill dosage form contains 4500 IU lipase.

The compositions or dosage forms (e.g., tablets or capsules) of the present invention can be stored in any suitable package. For example, the package can be a glass or plastic jar with a threaded or press-fit closure. Alternatively, the compositions or dosage forms of the present invention can be packaged as a unit dosage form in "blister packs". Applicants have found that improved stability of the digestive enzyme compositions or dosage forms can be provided by providing a moisture-proof seal, and/or a moisture-proof package. Non-limiting examples of suitable moisture-proof packages include glass jars, plastic jars incorporating moisture barrier resins or coatings, aluminized plastic (e.g., Mylar) packaging, etc. The term "moisture-proof" refers to a package which has a permeability to water of less than about 0.5 mg water per $cm^3$ of container volume per year.

Containers (e.g., bottles) can be closed with any suitable closure, especially closures which minimize the ingress of moisture during storage. For example, the compositions or dosage forms of the present invention can be closed with a closure such as Saf-Cap III-A (Van Blarcom Closures, Inc.), containing HS 035 Heat Seal/20F (SANCAP Liner Technology, Inc.) printed as a sealing liner.

In order to ensure package integrity and minimize moisture ingress during storage, sealed packages containing the compositions or dosage forms of the present invention can be leak-tested after dispensing the composition or dosage form of the present invention and sealing the package. For example, the sealed packages can be tested by applying a controlled vacuum to the closure, and detecting the decrease in vacuum over time. Suitable leak-testing equipment includes those manufactured by Bonfiglioli (e.g., model LF-01-PKV or model PKV 516).

Packages containing the compositions or dosage forms of the present invention can also contain a desiccant (i.e., a substance which absorbs, reacts with, or adsorbs water) capable of reducing the humidity inside the package, for example a desiccant capsule, capable of "scavenging" moisture from the atmosphere sealed inside the package. Non-limiting examples of suitable dessicants which can be placed inside such packages include zeolites (e.g., molecular sieves such as 4 Å molecular sieves), clay (e.g., montmorillonite clay), silica gel, activated carbon, or combinations thereof. In one embodiment, the desiccant comprises molecular sieves.

In addition, it is common practice when packaging oral pharmaceutical unit doses to add a "plug" of a cellulosic material, such as cotton, into the top of the container to fill the empty space at the top of the container, thereby minimizing movement of the contents. Cellulosic materials are somewhat hygroscopic, and can act as a "reservoir" of moisture inside the package. Accordingly, in one embodiment of the packages of the present invention, no cellulosic or cotton "plug" is present in the package. In another embodiment of the packages of the present invention, the packages lack a cellulosic or cotton plug, and contain a desiccant.

The compositions of the present invention can be prepared using conventional techniques, but modified as indicated herein to provide moisture contents of about 3% or less, water activities of about 0.6 or less, or provide stabilized digestive enzyme compositions which exhibit a loss of activity of no more than about 15% after three months accelerated stability testing. For example, particles of digestive enzymes (e.g., pancrelipase) can be coated in a fluidized bed coating apparatus equipped with a dehumidifier. In one embodiment, the coating apparatus is operated in an atmosphere having a water content of about 4 $g/m^3$ or less, about 3.5 $g/m^3$ or less, about 3 $g/m^3$ or less, about 2.5 $g/m^3$ or less, about 2.0 $g/m^3$ or less, about 1.5 $g/m^3$ or less, about 1.0 $g/m^3$ or less, or about 0.5 $g/m^3$ or less, including all ranges and subranges therebetween. The atmosphere in which the coating is carried out can comprise dehumidified air, dehumidified nitrogen, or another dehumidified inert gas.

The coating can be applied as a solution of the enteric polymer (and optionally a suspended inorganic material) in an organic solvent such as an alcohol (e.g. ethanol), a ketone (e.g. acetone), methylene chloride, or mixtures thereof (e.g. mixtures of acetone ethanol).

The compositions of the present invention provide improved absorption of fats, proteins, and carbohydrates in patients suffering from conditions or disorders associated with a digestive enzyme deficiency. In one embodiment, compositions of the invention, in particular pancrelipase or pancreatin compositions, may be used to treat exocrine pancreatic insufficiency (EPI) associated with various diseases. Such diseases include, but are not limited to cystic fibrosis (CF). In some embodiments, such compositions may substantially alleviate malabsorption (e.g. of fats) associated with EPI in cystic fibrosis patients and other patients, including pediatric patients. In some embodiments, such compositions may increase the coefficient of fat absorption (CFA) to at least about 85% or more in cystic fibrosis patients. Such results may be achieved when co-administered with other agents or compositions, or may be achieved without co-administration with other agents. In one embodiment, such CFA results are achieved without co-administration of proton pump inhibitors such as Prilosec®, Nexium®, and the like.

For patients identified as having low GI pH levels (e.g., GI pH levels<about 4), improved results may be obtained by administering the compositions or dosage forms of the present invention together with proton pump inhibitors, antacids, and other drugs which increase the pH of the GI tract. For example, the compositions or dosage forms of the present invention can be administered separately from the proton pump inhibitors, antacid, or other drugs (either prior to, concurrently with, or after administration of the proton pump inhibitor, antacid, etc.). Alternatively, the proton pump inhibitor, antacid, or other drug can be combined with the pancreatin composition of the present invention as a single dosage form.

In yet another embodiment, the present invention provides a method of treating or preventing a disorder associated with a digestive enzyme deficiency comprising administering a composition of the present invention to a mammal in need thereof. In one embodiment, the mammal is a human.

In yet another embodiment, the present invention provides a method of treating or preventing a disorder associated with a digestive enzyme deficiency comprising administering a composition or dosage form of the present invention to a mammal in need thereof, wherein the composition or dosage form of the present invention comprises, in addition to at least one digestive enzyme, a proton pump inhibitor, antacid, or other medicament which increases GI pH. In still another embodiment, the present invention provides a method of treating or preventing a disorder associated with a digestive enzyme deficiency, comprising administering a composition or dosage form of the present invention, in combination with a dosage form comprising a proton pump inhibitor, antacid, or other medicament which increases GI pH.

Disorders which can be treated with the composition or dosage form of the present invention include conditions in which the patient has no or low levels of digestive enzymes or in which patients require digestive enzyme supplementation. For example, such conditions can include cystic fibrosis, chronic pancreatitis, other pancreatic diseases (e.g., hereditary, post-traumatic and allograft pancreatitis, hemochromatosis, Shwachman syndrome, lipomatosis, or hyperparathyroidism), side-effects of cancer or cancer treatment, side-effects of surgery (e.g., gastrointestinal bypass surgery, Whipple procedure, total pancreatectomy, etc.) or other conditions in which pancreatic enzymes cannot reach the intestine, poor mixing (e.g., Billroth II gastrectomy, other types of gastric by pass surgery, gastrinoma, etc.) side effects of drug treatments such as treatment with metformin or those drugs used to treat the symptoms of HIV and autoimmune diseases such as diabetes in which the pancreas may be compromised, obstruction (e.g., pancreatic and biliary duct lithiasis, pancreatic and duodenal neoplasms, ductal stenosis), malabsorption associated with celiac disease, food allergies and aging.

The amount of the composition or dosage form of the present invention administered daily to mammals (e.g., humans) depends upon the intended result. The skilled physician will be capable of prescribing the required dose based on his diagnosis of the condition to be treated.

For example, for the treatment of digestive enzyme insufficiency in humans (e.g., related to cystic fibrosis) the starting dose should be 500 to 1000 lipase units/kg/meal, with the total dose not exceeding 2500 lipase units/kg/meal or 4000 lipase units/g fat/meal in accordance with the recommendations of the US FDA. Typically, a patient should receive at least 4 dosage forms per day, preferably administered with food.

EXAMPLES

Example 1

Pancrelipase MT (minitablets) is a blend of pancrelipase raw material (e.g., obtained from Nordmark) and excipients (e.g., croscarmellose sodium, hydrogenated castor oil, colloidal silicon dioxide, microcrystalline cellulose, and magnesium stearate; Table 34) tabletted using round 2 mm diameter beveled punches. The physical characteristics of the Pancrelipase MT before coating are shown below in Table 1.

TABLE 1

| | |
|---|---|
| Diameter | 2.0 mm |
| Weight (of 10 MT) | 0.074-0.086 g |
| Thickness (mean value of 10 MT) | 2.2 ± 0.2 mm |
| Hardness | 0.5-2.0 Kp |
| Friability* (20 g of MT-30 min at 25 rpm) | 0.0-2.5% |

*USP method

Pancrelipase MT was coated with a coating formulation (Table 2) using a fluidized bed Glatt-GPCG1 apparatus equipped with a Munters ML 1350 dehumidifier in the process airflow. The coating process was carried out with process air at three different moisture contents (Table 3). For each batch, the coating weight was approximately 15% of the total weight of the coated particles. The composition of the coated particles for each set a process conditions is approximately the same (Table 4), and appeared uniform, smooth and homogeneous after microscopic examination.

TABLE 2

| Material | % (w/w) |
|---|---|
| Hypromellose Phthalate (HP55) | 10.19 |
| Triethyl citrate (TEC) | 1.02 |
| Talc | 1.02 |
| Ethanol 96% | 79.78 |
| Acetone | 7.99 |
| | 100.00 |

TABLE 3

| Lot | Process Air Moisture Content (g/m$^3$) |
|---|---|
| P9A165 | 8.8 |
| P9A167 | 0.4 |
| P9A170 | 3.6 |

TABLE 4

| Material | Coating Composition % (w/w) |
|---|---|
| Pancrelipase MT | 85.00 |
| Hypromellose Phthalate (HP55) | 12.50 |
| Triethyl citrate (TEC) | 1.25 |
| Talc | 1.25 |
| | 100.00 |

The three sets of samples (i.e., P9A165, P9A167, and P9A170) showed residual moisture contents corresponding to the moisture content of the processing air flow (Table 4).

TABLE 5

| Lot | Loss on Drying (%) |
|---|---|
| P9A165 | 2.8 |
| P9A167 | 1.1 |
| P9A170 | 1.7 |

The influence of residual moisture on the loss of activity over time was evaluated under accelerated stability conditions as follows:

Hard gelatin capsules (dosage 20,000 IU Lipase) were filled with the three lots of coated Pancrelipase MT minitablets described above and stored at 40° C. at 75% relative humidity in sealed Nialene bags.

Lipase activity was evaluated after 15 days and 4 months of storage. The results are shown in Table 6.

TABLE 6

| Batch | LoD | Time zero | 15 days Lipase (IU/mg) | 4 months |
|---|---|---|---|---|
| P9A165 | (2.8%) | 62.5 | 46 (−26% activity) | 33.6 (−46% activity) |
| P9A167 | (1.1%) | 64.5 | 53 (−18% activity) | 46.2 (−28% activity) |
| P9A170 | (1.7%) | 63.8 | 53 (−17% activity) | 44.8 (−30% activity) |

The results of Table 6 show that improved stability is provided by compositions having a moisture content of less than about 2%. Alternatively, improved stability is provided by coating under an atmosphere with a moisture content of less than 3.6 g/m$^3$ to 0.4 g/m$^3$.

Example 2

Pancrelipase MT particles were coated with two coating compositions containing different amounts of talc (Table 7).

TABLE 7

| | Composition % (w/w) | |
|---|---|---|
| Material | Low talc content | High talc content |
| Hypromellose Phthalate (HP55) | 10.190 | 5.825 |
| Triethyl citrate (TEC) | 1.020 | 0.580 |
| Talc | 1.020 | 5.825 |
| Ethanol 96% | 79.780 | 79.780 |
| Acetone | 7.990 | 7.990 |
| | 100.000 | 100.000 |
| HP:TEC:Talc ratio | 10:1:1 | 10:1:10 |
| Total solid content | 12.23% | 12.23% |

Coating trials were carried out using a fluidized bed Glatt-GPCG1 apparatus equipped with a Munters ML 1350 dehumidifier in order to assure process air flow at a low moisture content (i.e., lower than 1 g/m$^3$). Coating weights were approximately 15%. The theoretical composition of the two batches is reported in Table 8. Microscopic examination indicated that the coatings on all samples were smooth and homogeneous. Residual moisture contents were measured by loss on drying (Table 9).

TABLE 8

| | Batch | |
|---|---|---|
| | P9A230 Low talc content | P9A240 High talc content |
| Material | Composition % (w/w) | |
| Pancrelipase MT | 85.000 | 85.000 |
| Hypromellose Phthalate (HP55) | 12.500 | 7.143 |
| Triethyl citrate (TEC) | 1.250 | 0.714 |
| Talc | 1.250 | 7.143 |
| | 100.000 | 100.000 |

TABLE 9

| Lot | Loss on Drying (%) |
|---|---|
| P9A230 | 0.9 |
| P9A240 | 0.9 |

The effects of the different coating compositions on the loss of activity over time were evaluated under accelerated stability conditions as follows:

Hard gelatin capsules (dosage 20,000 IU Lipase) were filled with the two lots of coated Pancrelipase MT described above, and stored at 40° C. and 75% relative humidity in sealed Nialene bags.

Lipase activity was checked after 1, 2 and 3 months of storage as shown in Table 10.

TABLE 10

| Batch | Time zero | 1 month | 2 months | 3 months |
|---|---|---|---|---|
| | | Lipase (IU/mg) | | |
| P9A230 Low talc content | 64.5 | 57.6 (−11% activity) | 49.6 (−23% activity) | 52.3 (−19% activity) |
| P9A240 High talc content | 65.3 | 58.2 (−11% activity) | 60.62 (−7% activity) | 59.6 (−9% activity) |

The results showed that the loss of activity after three months of storage under accelerated stability conditions is significantly lower for samples coated with a high talc content coating (Lot P9A240). Accordingly, increasing the talc concentration from approximately 1% to approximately 7% results in significant improvements in enzyme stability.

Example 3

The effects of coating composition solvent was evaluated by preparing "high talc" and "low talc" coating compositions similar to those described in table 6, except that the ethanol (96% ethanol, 4% water)/acetone solvent was replaced with 100% acetone (Table 11).

TABLE 11

| | Composition % (w/w) | |
|---|---|---|
| Material | Low talc content | High talc content |
| Hypromellose Phthalate (HP55) | 10.190 | 5.825 |
| Triethyl citrate (TEC) | 1.020 | 0.580 |
| Talc | 1.020 | 5.825 |
| Acetone | 87.770 | 87.770 |
| | 100.000 | 100.000 |
| HP:TEC:Talc ratio | 10:1:1 | 10:1:10 |
| Total solid content | 12.23% | 12.23% |

The coating trials were carried out using a fluidized bed Glatt-GPCG1 apparatus equipped with a Munters ML 1350 dehumidifier in order to assure process air flow at a low moisture content (lower than 1 g/m$^3$). Coating weights were approximately 15%. The theoretical composition of the two batches is reported in Table 12.

TABLE 12

| | Batch | |
|---|---|---|
| | P9A318 Low talc content | P9A352 High talc content |
| Material | Composition % (w/w) | |
| Pancrelipase MT | 85.000 | 85.000 |
| Hypromellose Phthalate (HP55) | 12.500 | 7.143 |
| Triethyl citrate (TEC) | 1.250 | 0.714 |
| Talc | 1.250 | 7.143 |
| | 100.000 | 100.000 |

Lot P9A318 complied with commercial product specifications, but Lot P9A352 did not pass a gastro-resistance test. Microscopic examination showed that the film coating of Lot P9A352 was not as smooth and homogeneous as other coated samples, probably because of the higher evaporation rate of acetone compared with the ethanol/acetone mixture used in previous samples, and the high talc concentration in the coating.

Lot P9A318 was then evaluated under accelerated stability conditions as follows:

Hard gelatin capsules (dosage 20,000 IU Lipase) were prepared and stored at 40° C. and 75% relative humidity in sealed Nialene bags. Lipase activity was measured after 1, 2 and 3 months of storage as shown in Table 13.

TABLE 13

| Batch | Time zero | 1 month | 2 months | 3 months |
|---|---|---|---|---|
| | | Lipase (IU/mg) | | |
| P9A318 Low talc content | 63.6 | 59.5 (−6% activity) | 60.4 (−5% activity) | 55.4 (−13% activity) |

The stability of Lot P9A318 is significantly improved compared to the stability of Lot P9A230, which was prepared with a similar coating under similar coating conditions (Table 14). It therefore appears that replacement of 96% ethanol with acetone in the coating formulation provides a significantly lower loss of enzyme activity over time.

TABLE 14

| | Accelerated stability at 40° C. + 75% R.H. | | | 1 month | 2 months | 3 months |
|---|---|---|---|---|---|---|
| Lot | HP:TEC:Talc | Talc content | Solvent | Lipase (loss of activity) | | |
| P9A230 | 10:1:1 | Low | Ethanol\Acetone | −11% | −23% | −19% |
| P9A240 | 10:1:10 | High | Ethanol\Acetone | −11% | −7% | −9% |
| P9A318 | 10:1:1 | Low | Acetone | −6% | −5% | −13% |

Example 4

CPS gelatin and HPMC (hydroxypropylmethylcellulose) capsules were filled with identical coated lipase compositions. The water content of gelatin capsules is approximately 14%, and the water content of HPMC capsules is approximately 4%. In addition one set of HPMC capsules was dried to a moisture level of less than 2%. All samples were subjected to accelerated stability conditions (40° C. and 75% relative humidity; samples heat-sealed in Nialene bags, and lipase activity was tested after 15, and 90 days. The results are shown below in Tables 15-17.

1) HPMC CPS vs Gelatin CPS

TABLE 15

| | LOT P200450287 LOSS OF LIPASE ACTIVITY % | |
|---|---|---|
| TIME | CPS GELATIN | CPS HPMC (not dried) |
| 15 days | −12% | −3% |
| 30 days | −21% | −13% |

TABLE 16

| | LOT P200450614 LOSS OF LIPASE % | |
|---|---|---|
| TIME | GELATINE CPS | HPMC CPS (dried) |
| 30 days | −11 | −1 |

TABLE 17

| | LOT P200450653 LOSS OF LIPASE % | |
|---|---|---|
| TIME | GELATINE CPS | HPMC CPS (not dried) |
| 30 days | −14 | −8 |
| 90 days | −32 | −18 |

As shown in Tables 15-17, lipase compositions in HPMC capsules show significantly higher lipase activity after storage for 15, 30, and 90 days under accelerated stability conditions and dried HPMC capsules offer better stability than those which contain equilibrium moisture levels.

Example 5

Gelatin and hydroxypropylmethylcellulose capsules were filled with coated lipase compositions Minitablet form. The coating for the compositions of the gelatin capsules (P200050) contained approximately 10% talc, whereas the coating for the compositions of the hydroxypropylmethylcellulose capsules (P200550) contained approximately 33% talc. The coating compositions were otherwise identical. The following Table 18 compares the levels of degradation observed after storage under accelerated stability conditions with the moisture content of the compositions. As shown in Table 18, higher levels of lipase activity correlate with lower levels of moisture in the composition. In addition, compositions filled in HPMC capsules are more stable than compositions filled in to gelatin capsules.

TABLE 18

| | | % activity months 40° C./75% RH | | | | LOD % months 40° C./75% RH | | | |
|---|---|---|---|---|---|---|---|---|---|
| | | 0 | 1 | 3 | 6 | 0 | 1 | 3 | 6 |
| HPMC Batch | | | | | | | | | |
| P200550 | 503 | 100 | 100 | 105 | 101 | 1.6 | 1.7 | 1.6 | 1.5 |
| P200550 | 865 | 100 | 96 | 101 | 102 | 1.7 | 2.1 | 1.6 | 1.8 |
| P200550 | 500 | 100 | 102 | 101 | 98 | 0.8 | 1.9 | 1.7 | 2 |
| P200550 | 861 | 100 | 97 | 103 | 99 | 1.5 | 1.7 | 2.0 | 1.4 |
| P200550 | 502 | 100 | 100 | 99 | 98 | 0.4 | 1.4 | 2.3 | 2.0 |
| P200550 | 859 | 100 | 103 | 103 | 97 | 1.1 | 0.7 | 1.9 | 1.3 |
| Average | | 100 | 100 | 102 | 99 | 1.2 | 1.6 | 1.9 | 1.7 |
| Gelatin Batch | | | | | | | | | |
| P200050 | 981 | 100 | 90 | 92 | 81 | 2.9 | 3.0 | 3.0 | 2.8 |
| P200050 | 975 | 100 | 89 | 79 | 66 | 2.7 | 3.2 | 3.1 | 2.8 |
| P200050 | 977 | 100 | 96 | 93 | 87 | 3.2 | 3.4 | 3.2 | 2.9 |
| Average | | 100 | 92.5 | 86 | 77 | 3.0 | 3.3 | 3.2 | 2.9 |

Example 6

The effects of storing capsules containing lipase compositions in packages containing a desiccant were evaluated by measuring lipase activity in the samples after 30 and 90 days of storage under accelerated stability conditions (40° C. and 75% relative humidity; samples heat-sealed in Nialene bags). As shown in Tables 19 and 20, lipase activity is significantly higher in packages containing a desiccant and in capsules that are dried below their equilibrium moisture content.

2) Desiccants
Desiccant 1: silica gel in Tyvek® bags
Desiccant 2: molecular sieves in Tyvek® bags

TABLE 19

| | LOSS OF LIPASE % | | |
|---|---|---|---|
| TIME | P200450614 in HPMC cps (dried) no desiccant | P200450614 in HPMC cps (dried) desiccant 1 | P200450614 in HPMC cps (dried) desiccant 2 |
| 30 days | −1 | +4 | +1 |
| 90 days | −10 | +2 | 0 |

TABLE 20

| | LOSS OF LIPASE % | | |
|---|---|---|---|
| TIME | P200450653 in HPMC cps no desiccant | P200450653 in HPMC cps desiccant 1 | P200450653 in HPMC cps desiccant 2 |
| 30 days | −8 | −8 | −5 |
| 90 days | −18 | −14 | −10 |

Example 7

Pancrelipase MT particles were coated with two coating compositions having a level of talc intermediate between the "low" and "high" levels employed above (HP55:TEC:Talc=10:1:5), using either acetone or a mixture of ethanol/acetone as the coating solvent. The theoretical composition of the two coating suspensions shown in Table 21, below.

TABLE 21

| | Composition % (w/w) | |
|---|---|---|
| Material | Intermediate talc content | |
| Hypromellose Phthalate (HP55) | 7.644 | 7.644 |
| Triethyl citrate (TEC) | 0.764 | 0.764 |
| Talc | 3.822 | 3.822 |
| Ethanol | 79.780 | |
| Acetone | 7.990 | 87.770 |
| | 100.000 | 100.000 |
| HP:TEC:Talc ratio | 10:1:5 | 10:1:5 |
| Total solid content | 12.23% | 12.23% |

The coating trials were carried out using a fluidized bed Glatt-GPCG1 apparatus equipped with a Munters ML 1350 dehumidifier in order to assure process air flow at a low moisture content (lower than 1 g/m$^3$).

The batches were prepared by coating the Pancrelipase MT at a coating weight of approximately 15%. Three batches were prepared with an ethanol/acetone coating solvent and three batches were prepared with an acetone coating solvent. The theoretical composition, which was the same for all six batches, is shown below in Table 22.

TABLE 22

| | Batch | |
|---|---|---|
| | P9A483-P9A485-P9A486 Ethanol/Acetone as solvent | P9A405-P9A476-P9A477 Acetone as solvent |
| Material | Composition % (w/w) | |
| Pancrelipase MT | 85.00 | 85.00 |
| Hypromellose Phthalate (HP55) | 9.37 | 9.37 |
| Triethyl citrate (TEC) | 0.94 | 0.94 |
| Talc | 4.69 | 4.69 |
| | 100.00 | 100.00 |

Microscopic examination of the coating for all six samples appeared smooth and homogeneous. The coated Pancrelipase MT particles were then filled into HPMC capsules and packaged in glass bottles containing desiccants (molecular sieves). The bottles were then sealed, stored under accelerated stability conditions and lipase activity was evaluated at various time periods as indicated below in Table 23.

The packaging conditions for each sample was as follows. Twelve HPMC capsules (dosage 20,000 IU Lipase) and 1 g of molecular sieves (Minipax sorbent-Multisorb) as desiccant were put in a 30 mL capacity glass bottle. The bottles were closed with Saf-Cap III-A, containing HS 035 Heat Seal/20F printed as a sealing liner and stored at 40° C./75% RH.

TABLE 23

| lot | Solvent | | Accelerated stability at 40° C. + 75% R.H. 0 days | 20 days | 30 days | 40 days | 60 days | 90 days | 120 days | 180 days |
|---|---|---|---|---|---|---|---|---|---|---|
| P9A483 | Ethanol\Acetone | Lipase U USP/mg | 69.0 | 67.0 | 72.4 | 62.6 | 64.7 | nd | nd | nd |
| | | % LOD | 1.0 | 0.5 | 0.2 | 0.2 | 0.6 | nd | nd | nd |
| | | Lipase (loss of activity) | | −3% | 5% | −9% | −6% | nd | nd | nd |
| P9A485 | Ethanol\Acetone | Lipase U USP/mg | 70.0 | 73.2 | 65.7 | 69.8 | 66.9 | nd | nd | nd |
| | | % LOD | 1.1 | 0.6 | 0.3 | 0.6 | 0.6 | nd | nd | nd |
| | | Lipase (loss of activity) | | 5% | −6% | 0% | −4% | nd | nd | nd |
| P9A486 | Ethanol\Acetone | Lipase U USP/mg | 63.0 | 61.4 | 59.7 | 62 | 61.5 | nd | nd | nd |
| | | % LOD | 1.6 | 0.2% | 0.6% | 0.5% | 0.4% | nd | nd | nd |
| | | Lipase (loss of activity) | | −3% | −5% | −2% | −2% | nd | nd | nd |
| P9A405 | Acetone | Lipase U USP/mg | 64.0 | 63.2 | 62.9 | 65.1 | 65.5 | 64.7 | 66.7 | 63.1 |
| | | % LOD | 1.3 | 0.3 | 0.3 | 0.3 | 0.4 | 0.04 | 0.6 | 0.2 |
| | | Lipase (loss of activity) | | −1% | −2% | 2% | 2% | 1% | 4% | −1% |
| P9A476 | Acetone | Lipase U USP/mg | 64.9 | 65.3 | 62.1 | 62.4 | 62.6 | 58.7 | 67.0 | 61.4 |
| | | % LOD | 1.2 | 0.4 | 1.0 | 1.3 | 0.5 | 1.0 | 1.0 | 0.6 |
| | | Lipase (loss of activity) | | 1% | −4% | −4% | −4% | −10% | 3% | −5% |
| P9A477 | Acetone | Lipase U USP/mg | 68.7 | 71.7 | 68.0 | 67.2 | 69.7 | 64.4 | 73.4 | 66.2 |
| | | % LOD | 1.1 | 0.2 | 0.3 | 1.0 | 0.0 | 0.6 | 0.7 | 0.4 |
| | | Lipase (loss of activity) | | 4% | −1% | −2% | 1% | −6% | 7% | −4% |

As shown in Table 23, the three samples prepared with the ethanol/acetone coating solvent showed similar losses in lipase activity. After 2 months of storage, two of the samples prepared with the acetone coating solvent did not exhibit any loss of activity, and the third showed a 4% of reduction of activity. This suggests that samples prepared with the acetone coating solvent are more stable than samples prepared with the ethanol/acetone coating solvent.

Example 8

Microtablets

To provide further choices for dosage formulations were made in which the dimensions of the tablets was significantly reduced. The pancrelipase blend was tabletted with round 1.5 mm diameter, 1.2 mm radius of curvature punches.

The compression parameters were set to obtain microtablets ("μT") with friability lower than 2.5% (USP method). The characteristics of Lot 9A402 are shown in Table 24.

TABLE 24

| Lot P9A402 | Values |
|---|---|
| Diameter | 1.5 mm |
| Weight (of 20 μT) | 0.071 g (0.070-0.073) |
| Thickness (as mean value of 20μT) | 1.73 mm (1.70-1.77) |

TABLE 24-continued

| Lot P9A402 | Values |
|---|---|
| Hardness (as mean value of 20μT) | 4 Newton (3-5) |
| Friability (20 g of μT-30 min at 25 rpm) | 1.80% |

Lot P9A402 was coated in a fluid bed Glatt-GPCG1 apparatus equipped with a Munters ML 1350 dehumidifier in order to assure process air flow at low moisture content (lower than 1 g/m$^3$) with a suspension having the composition shown in Table 2. A coating weight of 22% was obtained. Microscopic examination of the film coatings indicated that all of the samples appeared smooth and homogeneous.

The theoretical composition of the batch Lot P9A422 is shown in Table 25.

TABLE 25

| Lot P9A422 | Standard coat Composition % (w/w) |
|---|---|
| Pancrelipase MT | 78.00 |
| Hypromellose Phthalate (HP55) | 18.34 |
| Triethyl citrate (TEC) | 1.83 |
| Talc | 1.83 |
| | 100.000 |

Two other batches of microtablets were prepared as described above, and their properties are shown below in Table 26.

TABLE 26

| Characteristics | Lot P9A457 | Lot P9A459 |
|---|---|---|
| Diameter | 1.5 mm | 1.5 mm |
| Weight (of 20 µT) | 0.072 g (0.070-0.073) | 0.071 g (0.070-0.074) |
| Thickness (as mean value of 20µT) | 1.73 mm (1.67-1.83) | 1.74 mm (1.69-1.82) |
| Hardness (as mean value of 20µT) | 5 Newton (3-6) | 5 Newton (4-6) |
| Friability (20 g of µT-30 min at 25 rpm) | 1.99% | 2.02% |

Pancrelipase microtablets were coated with one of two suspensions having levels of talc intermediate between the "high" and "low" levels described above (HP55:TEC:Talc=10:1:5), using either acetone or a mixture of ethanol in acetone as a coating solvent (Table 27).

The six trials were carried out using a fluidized bed Glatt-GPCG1 apparatus equipped with a Munters ML 1350 dehumidifier in order to assure process air flow at low moisture content (lower than 1 g/m$^3$). Coating weights were approximately 22%, and microscopic examination indicated that the coatings were smooth and homogeneous.

TABLE 27

| Coated µT | Solvent | Uncoated µT |
|---|---|---|
| Lot. P9A460 | Acetone | Lot. P9A402 |
| Lot. P9A458 | Acetone | Lot. P9A457 |
| Lot. P9A463 | Acetone | Lot. P9A459 |
| Lot. P9A473 | Ethanol/Acetone | Lot. P9A402 |
| Lot. P9A466 | Ethanol/Acetone | Lot. P9A457 |
| Lot. P9A468 | Ethanol/Acetone | Lot. P9A459 |

The theoretical compositions of the batches are summarized in Table 28.

TABLE 28

| | Batch | |
|---|---|---|
| Material | P9A466-P9A468-P9A473 Ethanol/Acetone as solvent | P9A458-P9A460-P9A463 Acetone as solvent |
| | Composition % (w/w) | |
| Pancrelipase MT | 78.00 | 78.00 |
| Hypromellose Phthalate (HP55) | 13.75 | 13.75 |
| Triethyl citrate (TEC) | 1.37 | 1.37 |
| Talc | 6.88 | 6.88 |
| | 100.00 | 100.00 |

HPMC cps capsules were filled with the coated microtablets described above, and packed in glass bottles containing desiccants (molecular sieves). The bottles were then closed with Saf-Cap III-A, containing HS 035 Heat Seal/20F printed as a sealing liner and stored under accelerated stability conditions (40° C. and 75% relative humidity). Twelve HPMC capsules (dosage 5,000 IU Lipase) and 1 g of molecular sieves (Minipax sorbent-Multisorb) as desiccant were placed in a 30 mL capacity glass bottle. Lipase activity was measured at 20, 30, 40, and 60 days of storage as shown in Tables 29 and 30.

TABLE 29

| lot | Solvent | Accelerated stability at 40° C. + 75% R.H. | 0 days | 20 days | 30 days | 40 days | 60 days | 90 days | 120 days | 180 days |
|---|---|---|---|---|---|---|---|---|---|---|
| P9A466 | Ethanol\Acetone | Lipase U USP/mg | 64.7 | 67.0 | 64.6 | 63.6 | 62.3 | nd | nd | nd |
| | | % LOD | 1.7 | 2.2 | 0.4 | 0.0 | 0.0 | nd | nd | nd |
| | | Lipase (loss of activity) | | 4% | 0% | -2% | -4% | nd | nd | nd |
| P9A468 | Ethanol\Acetone | Lipase U USP/mg | 61.2 | 59.6 | 57.7 | 58.6 | 58.9 | nd | nd | nd |
| | | % LOD | 1.7 | 0.5 | 0.4 | 0.0 | 0.0 | nd | nd | nd |
| | | Lipase (loss of activity) | | 4% | 0% | -2% | -4% | nd | nd | nd |
| P9A473 | Ethanol\Acetone | Lipase U USP/mg | 59.8 | 58.9 | 57.7 | 59.4 | 58.4 | nd | nd | nd |
| | | % LOD | 1.8 | 0.7 | 0.9 | 0.0 | 0.0 | nd | nd | nd |
| | | Lipase (loss of activity) | | -2% | -4% | -1% | -2% | nd | nd | nd |
| P9A458 | Acetone | Lipase U USP/mg | 62.4 | 65.4 | 64.3 | 62.9 | 65.0 | 62.3 | 65.5 | 62.6 |
| | | % LOD | 3.0 | 0.1 | 0.5 | 0.0 | 0.0 | 0.6 | 1.3 | 0.3 |
| | | Lipase (loss of activity) | | 5% | 3% | 1% | 4% | 0% | 5% | 0% |
| P9A460 | Acetone | Lipase U USP/mg | 56.9 | 58.2 | 59.2 | 58.3 | 60.0 | 57.6 | 62.2 | 56.8 |
| | | % LOD | 1.7 | 0.07 | 0.3 | 0.0 | 0.0 | 0.0 | 0.6 | 0.2 |
| | | Lipase (loss of activity) | | 2% | 4% | 2% | 5% | 1% | 9% | 0% |

TABLE 29-continued

| Accelerated stability at 40° C. + 75% R.H. | | | 0 days | 20 days | 30 days | 40 days | 60 days | 90 days | 120 days | 180 days |
|---|---|---|---|---|---|---|---|---|---|---|
| lot | Solvent | | | | | | | | | |
| P9A463 | Acetone | Lipase U USP/mg | 62.7 | 63.8 | 62.2 | 61.5 | 59.8 | 54.5 | 62.6 | 58.6 |
| | | % LOD | 1.6 | 2.3 | 0.5 | 0.0 | 0.0 | 0.4 | 0.6 | 0.5 |
| | | Lipase (loss of activity) | | 2% | −1% | −2% | −5% | −13% | 0% | −7% |

TABLE 30

| Accelerated stability at 40° C. + 75% R.H. | | 20 days | 30 days | 40 days | 60 days |
|---|---|---|---|---|---|
| Lot | Solvent | Lipase (loss of activity) | | | |
| P9A466 | Ethanol\Acetone | +4% | 0% | −2% | −4% |
| P9A468 | Ethanol\Acetone | −3 | −4% | −4 | −4% |
| P9A473 | Ethanol\Acetone | −2% | −4% | −1% | −2% |
| P9A458 | Acetone | +5% | +3% | +1% | +4% |
| P9A460 | Acetone | +2 | +4% | +2% | +5% |
| P9A463 | Acetone | +2% | −1% | −2% | −5% |

All three samples prepared using an ethanol/acetone coating solvent showed similar behavior and after two months of storage, the loss of lipase activity was 2%-4%. After two months of storage the loss of activity of two of the samples prepared using an acetone coating solvent showed no evidence of loss of lipase activity, while the third sample showed a 5% decrease in lipase activity. Thus, compositions prepared with acetone as the coating solvent were more stable than samples prepared with an ethanol/acetone coating solvent, possibly linked to the water content of the ethanol used.

The microtablets prepared above were slightly oblong (see Tables 24 and 26); the ratio between the microtablet thickness and diameter was between 1.22:1 and 1.15:1.

To further reduce the dimensions of the microtablets, new samples were prepared with ratios of thickness to diameter ratio nearer to 1:1 (Lot Q9A006), are shown below in Table 31.

TABLE 31

| Characteristics | Lot Q9A006 |
|---|---|
| Diameter | 1.5 mm |
| Weight (of 20 μT) | 0.060 g (0.058-0.062) |
| Thickness (as mean value of 20μT) | 1.50 mm (1.45-1.58) |
| Hardness (as mean value of 20μT) | 5 Newton (4-6) |
| Friability (20 g of μT-30 min at 25 rpm) | 1.63% |

Lot Q9A006 was coated with the compositions shown in Table 32 at a coating weight of 22%. The coating trials were carried out using a fluid eyes bed Glatt-GPCG1 apparatus equipped with a Munters ML 1350 dehumidifier in order to assure processing air flow at low moisture content (lower than 1 g/m$^3$).

The theoretical composition of the coated microtablet Lot Q9A019 was the same as that shown in Table 28. Microscopic examination indicated that the coatings were smooth and homogeneous.

TABLE 32

| Material | Composition % (w/w) Intermediate talc content |
|---|---|
| Hypromellose Phthalate (HP55) | 7.644 |
| Triethyl citrate (TEC) | 0.764 |
| Talc | 3.822 |
| Acetone | 87.770 |
| | 100.000 |
| HP:TEC:Talc ratio | 10:1:5 |
| Total solid content | 12.23% |

The above examples show that digestive enzyme compositions with improved stability can be prepared by maintaining low moisture contents and water activities in the components of the composition, for example by replacing aqueous ethanol/acetone coating solvents with acetone, coating minitablets and microtablets in dehumidified process air flows (e.g., having moisture contents between 0.4 g/m$^3$ and 3.6 g/m$^3$). In addition, increased levels of inorganic materials in the coating (e.g., HP55:TEC:Talc ratios ranging from 10:1:1 to 10:1:5), selection of less hygroscopic capsule materials (e.g., HPMC or dried HPMC), and improved packaging techniques (e.g., storage in well-sealed glass bottles containing dessicants) provide digestive enzyme compositions and dosage forms with improved stability.

Example 9

The following Table 33 shows accelerated stability testing (in bottles; 40° C. and 75% Relative Humidity) of Eudragit coated pancrelipase Minitabs.

TABLE 33

| | Batch | | | | | | | | | |
|---|---|---|---|---|---|---|---|---|---|---|
| | 1 | | 2 | | 3 | | 4 | | 5 | |
| | Time (months) | | | | | | | | | |
| | 0 | 1 | 0 | 1 | 0 | 1 | 0 | 1 | 0 | 1 |
| Lipase IU | 23030 | 15510 | 24180 | 15810 | 23550 | 16014 | 23000 | 16100 | 23613 | 17594 |
| % (Vs time 0) | 100 | 67 | 100 | 65 | 100 | 68 | 100 | 70 | 100 | 74 |
| L.o.D. % (max. 5.0) | 4.0 | 4.9 | 3.9 | 4.6 | 4.2 | 4.2 | 3.9 | 4.3 | 3.3 | 3.7 |

The results indicate that conventional enteric coatings such as Eudragit do not provide stabilized pancrelipase compositions.

Example 10

Examples of dosage forms comprising ER coated beads of varying dosage per capsule, coated as described in previous examples, are shown in Table 34, below:

TABLE 34

| Component | Composition 1 (µT) | Composition 2 (MT) | Composition 3 (MT) | Composition 4 (MT) |
|---|---|---|---|---|
| µT or MT | | | | |
| Pancrelipase | 55.7 (5,000 USP units) | 108.9 (10,000 USP units) | 163.4 (15,000 USP units) | 217.8 (20,000 USP units) |
| Croscarmellose Sodium | 1.9 | 3.6 | 5.5 | 7.3 |
| Hydrogenated Castor Oil | 0.6 | 1.2 | 1.8 | 2.4 |
| Colloidal Silicon Dioxide | 0.3 | 0.6 | 0.9 | 1.2 |
| Cellulose Microcrystalline | 3.1 | 6.1 | 9.1 | 12.1 |
| Magnesium Stearate | 0.3 | 0.6 | 0.9 | 1.2 |
| Coating | | | | |
| Hypromellose Phthalate | 12.2 | 18.9 | 28.4 | 37.8 |
| Talc | 6.1 | 9.5 | 14.2 | 18.9 |
| Triethyl Citrate | 1.2 | 1.92 | 2.8 | 3.8 |
| Acetone[b] | Trace | Trace | Trace | Trace |
| Capsule | | | | |
| Carrageenan | 0.1 | 0.2 | 0.3 | 0.3 |
| Potassium Chloride | 0.2 | 0.3 | 0.4 | 0.4 |
| Titanium Dioxide | 2.3 | 3.5 | 5.1 | 5.2 |
| Hypromellose | 33.5 | 52.9 | 79.4 | 79.2 |
| Carnauba Wax | Trace | Trace | Trace | Trace |
| Water | 0.38 | 0.60 | 0.9 | 0.90 |
| Yellow Iron Oxide | — | 0.1 | — | 0.2 |
| Red Iron Oxide | — | — | 0.3 | — |
| FDC Blue 2 | — | — | — | 0.1 |

Example 11

The following Table 35 shows the water content of various sized containers containing capsules comprising the compositions of the present invention. The water content includes total water from the capsules, and water permeating into the container over a two-year storage time. The "equivalent molecular sieves weight" is the minimum amount of molecular sieves required to absorb the water present in the containers.

TABLE 35

| Bottle sizes (cc) | Cps n° | Cps weight (mg) | Cps. moisture (%) | Total water from cps (mg/bottle) | Water from Permeation. (mg/2y/bottle) | Equivalent Molec. Sieves weight (g) |
|---|---|---|---|---|---|---|
| 30 | 12 | 95 | 3% | 34 | 111 | 0.96 |
| 200 | 100 | 95 | 3% | 285 | 401 | 4.58 |
| 750 | 500 | 95 | 3% | 1425 | 474 | 12.66 |
| 30 | 20 | 95 | 3% | 57 | 111 | 1.12 |

Example 12

A Phase III randomized, double-blind, placebo-controlled, cross over study was carried out to compare the effects of treatment with the pancrelipase compositions of Table 34 to that of a placebo in 34 CF patients with EPI aged seven years and older. The study was conducted in 14 CF centers throughout the US. The primary endpoint of the study compared the coefficient of fat absorption following oral administration of the pancrelipase composition in daily doses less than or equal to 10,000 lipase units per kilogram of body weight in combinations of 5,000, 10,000, 15,000 or 20,000 lipase units per capsule versus a placebo. The secondary endpoints of the trial evaluated changes in the coefficient of nitrogen absorption as a determinant of protein absorption, cholesterol, fat soluble vitamins, weight, body mass index and EPI symptoms.

Patients treated with these compositions showed a statistically significant increase in the coefficient of fat absorption and coefficient of nitrogen absorption as compared to those receiving a placebo and had fewer symptoms associated with impaired absorption such as bloating, flatulence, pain and evidence of fat in stools. Increases in mean cholesterol and vitamin levels were also observed in patients taking these pancrelipase compositions versus placebo. A statistically significant decrease was obtained in the frequency of stools per day. These compositions were well tolerated by patients, and no drug related serious adverse events were observed during the study.

The mean percentage coefficient of fat absorption in patients receiving these compositions was 88.28% versus 62.76% in patients receiving placebo. The mean percentage coefficient of nitrogen absorption was 87.2% versus 65.7% in patients taking placebo and the mean number of stools per day decreased in respective patient groups from 2.66 to 1.77.

Example 13

A pediatric, Phase III clinical trial was carried out to evaluate the effects of treatment with the compositions of Table 34 in an open-label study in 19 CF patients under the age of seven in 11 CF treatment centers in the US—the first pancreatic replacement therapy trial of this size conducted on young children and infants with exocrine pancreatic insufficiency. The study design involved a seven-day dose stabilization period followed by a seven-day treatment period; patients received 5,000 lipase units per capsule daily, with the product being sprinkled on food as required. The study's primary endpoint was the percentage of "responders," or those patients without excess fat in stools and without signs and symptoms of malabsorption after one and two weeks of treatment. Secondary endpoints included weight change, nutritional status, stool frequency and consistency, incidences of bloating, pain and flatulence as well as physician and parent or guardian judgment of clinical symptoms improvement. Product safety was also assessed.

The mean percentage of responders, as defined in the study protocol, at screening (the beginning of the stabilization period when patients were on a previous pancreatic enzyme replacement therapy and prior to treatment) was 52.6%. At the end of the stabilization period and the end of the treatment period, the mean percentages of responders were 66.4% and 57.9% respectively. Among the children in the study, malabsorption symptoms were significantly lower at the end of the treatment period than at screening, consistent with observations regarding control of malabsorption symptoms seen in the Phase III trial described in Example 12, above. The pancrelipase compositions of the present invention were also well tolerated by these patients and no drug related serious adverse events were observed during the trial.

The results showed that the compositions of the present invention effectively controlled the signs and symptoms of malabsorption and support the results obtained in the pivotal phase III trial described in Example 12. A significant proportion of physicians and patients felt that the control of symptoms with the compositions of the present invention was improved versus previous therapies.

Example 14

A Phase III opened-label, randomized, single center, single treatment, cross-over study was carried out to compare the effects of treatment with the pancrelipase compositions of Table 34 to determine the gastrointestinal bioavailability of these compositions in fed conditions in 10 chronic pancreatitis patients with exocrine pancreatic insufficiency. Exclusionary drugs (proton pump inhibitors (PPI's), antacids, and drugs capable of altering GI mobility were discontinued 7 days prior to entering the study. Patients were randomized to receive either Ensure Plus™ (a vitamin fortified nutritional supplement available from Abbott) alone or Ensure Plus™ in combination with 75,000 USP lipase units (3 capsules containing 20,000 units each plus 3 capsules containing 5000 units each) per procedure. The capsules were opened and their contents mixed with 480 mL of Ensure Plus™ immediately before administration. After a one-day washout period, this procedure was repeated, except that patients who previously received Ensure Plus™ alone received Ensure Plus™ in combination with 75,000 USP lipase units, and patients who previously received the combination of Ensure Plus™ and lipase, received Ensure Plus™ alone. The following day, patients received a physical exam, and blood and urine samples were collected. The bioavailability of the compositions of the present invention was estimated from the amount of the respective enzymes released and recovered (i.e., lipase, amylase, and chymotrypsin) in the duodenum following administration of the composition in the presence of Ensure Plus™. Measurements of cholecystokinin levels in the blood, and gastric and duodenal pH were also measured. Lipase activity was measured according to the method of Carriere, F.; Barrowman, J. A.; Verger, R.; Laugier, R. Secretion and contribution to lipolysis of gastric and pancreatic lipases during a test meal in humans. Gastroenterology 1993, 105, 876-88. Amylase and chymotrypsin were measured according to the methods described in Carriere, F.; Grandval, P.; Renou, C.; Palomba, A.; Prieri, F.; Giallo, J; Henniges, F.; Sander-Struckmeier, S.; Laugier, R. Quantitative study of digestive enzyme secretion and gastrointestinal lipolysis in chronic pancreatitis Clin. Gastroenterol. Hepatol. 2005, 3, 28-38.

Treatment with the pancrelipase compositions of the present invention was found to result in statistically significant greater amounts of amylase, lipase and chymotrypsin released in the duodenum of patients that received the combination of Ensure Plus™ and pancrelipase, compared to patients that received Ensure Plus™ only (after correcting for pH as a confounding factor).

The mean bioavailability for lipase, amylase and chymotrypsin for the eight patients who completed the study according to the protocol) was 27.5%, 21.6%, and 40.1% respectively. It was found that the patients fell into two different GI pH subpopulations ("normal pH" and "low pH"). For patients who had "normal pH" values (i.e., patients with a mean duodenal pH greater than 4), the mean bioavailability of lipase, amylase and chymotrypsin was higher than for the entire study group: 45.6%, 26.9%, and 47.7%, respectively. No difference in cholecystokinin values between the two treatments was observed.

Because the bioavailability for lipase, amylase, and chymotrypsin differs for "normal pH" and "low pH" patients (particularly for lipase), the efficacy of the pancrelipase compositions or dosage forms of the present invention can be enhanced, e.g., in "low pH" patients, by co-administration of medications which increase GI pH, for example PPI's and antacids. However, the compositions or dosage forms of the present invention can be administered without co-administration of e.g., PPI's.

The foregoing description of the invention has been presented for the purpose of illustration and description. It is not intended to be exhaustive or to limit the invention to the precise form disclosed. Modifications and variations are possible in light of the above teachings. The descriptions of the embodiments were chosen in order to explain and to describe the principles of the present invention and its practical application, and are not meant to be limiting on the scope of the claims.

All publications and patents or patent applications cited herein are incorporated by reference in their entirety to the same extent as if each individual publication, patent, or patent application were specifically and individually indicated incorporated by reference.

We claim:

1. A method of preparing a pancrelipase composition comprising a plurality of particles comprising pancrelipase, wherein each said particle is coated with an enteric coating, comprising the steps of:
coating the particles in an atmosphere wherein the atmosphere has a moisture content of about 3.6 g water per $m^3$ or less, with a coating comprising an enteric polymer and at least one inorganic material, thereby forming a plurality of enterically coated particles wherein the particles have a moisture content of about 3% or less.

2. The method of claim 1, wherein the atmosphere comprises air, nitrogen, or an inert gas.

3. The method of claim 1, wherein the particles are coated with a mixture comprising an enteric polymer dissolved in acetone and at least one inorganic material.

4. A method of preparing a pancrelipase composition comprising a plurality of particles comprising pancrelipase, wherein each said particle is coated with an enteric coating, comprising:

coating the particles in an atmosphere wherein the atmosphere has a moisture content of about 3.6 g water per $m^3$ or less, with a coating comprising an enteric polymer and at least one inorganic material, thereby forming a plurality of enterically coated particles wherein the particles have a water activity of about 0.6 or less.

5. The method of claim 4, wherein the atmosphere comprises air, nitrogen, or an inert gas.

6. The method of claim 4, wherein the particles are coated with a mixture comprising an enteric polymer dissolved in acetone and at least one inorganic material.

7. The method of claim 1, wherein the particles exhibit a loss of digestive enzyme activity of no more than 25% after six months of accelerated stability testing.

8. The method of claim 7, wherein the atmosphere comprises air, nitrogen, or an inert gas.

9. The method of claim 7, wherein the particles of pancrelipase are coated with a mixture comprising an enteric polymer dissolved in acetone and at least one inorganic material.

10. The method of claim 3, wherein the enteric polymer is hydroxypropylmethylcellulose phthalate and the inorganic material is talc.

11. The method of claim 6, wherein the enteric polymer is hydroxypropylmethylcellulose phthalate and the inorganic material is talc.

12. The method of claim 9, wherein the enteric polymer is hydroxypropylmethylcellulose phthalate and the inorganic material is talc.

13. The method of claim 1, wherein the moisture content is about 0.5 g water per $m^3$ or less.

14. The method of claim 4, wherein the moisture content is about 0.5 g water per $m^3$ or less.

15. The method of claim 7, wherein the moisture content is about 0.5 g water per $m^3$ or less.

16. The method of claim 7, wherein the loss of digestive enzyme activity is no more than 15% after six months of accelerated stability testing.

17. The method of claim 7, wherein the loss of digestive enzyme activity is no more than 12% after six months of accelerated stability testing.

18. The method of claim 7, wherein the loss of digestive enzyme activity is no more than 10% after six months of accelerated stability testing.

19. The method of claim 7, wherein the loss of digestive enzyme activity is no more than 8% after six months of accelerated stability testing.

20. The method of claim 7, wherein the loss of digestive enzyme activity is no more than 5% after six months of accelerated stability testing.

* * * * *